United States Patent
Antony et al.

(10) Patent No.: US 11,114,194 B2
(45) Date of Patent: Sep. 7, 2021

(54) NETWORK-BASED SYSTEMS AND METHODS FOR PROVIDING READMISSION NOTIFICATIONS

(71) Applicant: Audacious Inquiry LLC, Catonsville, MD (US)

(72) Inventors: Sandeep Antony, Columbia, MD (US); Scott Afzal, Washington, DC (US); Evan Carter, Washington, DC (US); Christopher Brandt, Baltimore, MD (US); Yedong Tang, Columbia, MD (US)

(73) Assignee: Audacious Inquiry, Catonsville, MD (US)

( * ) Notice: Subject to any disclaimer, the term of this patent is extended or adjusted under 35 U.S.C. 154(b) by 749 days.

(21) Appl. No.: 14/872,445

(22) Filed: Oct. 1, 2015

(65) Prior Publication Data
US 2017/0098043 A1  Apr. 6, 2017

(51) Int. Cl.
*G16H 40/20* (2018.01)
*G16H 10/60* (2018.01)

(52) U.S. Cl.
CPC ............ *G16H 40/20* (2018.01); *G16H 10/60* (2018.01)

(58) Field of Classification Search
None
See application file for complete search history.

(56) References Cited

U.S. PATENT DOCUMENTS 7,899,545 B2  3/2011  John
8,069,135 B2  11/2011  Fletcher et al.
(Continued)

FOREIGN PATENT DOCUMENTS

WO  WO-2015057715 A1 *  4/2015  ............ G16H 50/30

OTHER PUBLICATIONS

Alexander, Alex et al., Department of Health & Human Services, Improving Hospital Transitions and Care Coordination Using Automated Admission, Discharge and Transfer Alert https://www.healthit.gov/sites/default/files/onc-beacon-1 (Year: 2013).*

(Continued)

*Primary Examiner* — Rachelle L Reichert
(74) *Attorney, Agent, or Firm* — Ryan Alley IP (57) ABSTRACT

Networks and methods include receiving healthcare information and with a computer identifying when a patient is readmitted to a healthcare provider. A readmission notification is generated for identified readmissions. The notification may identify the patient being readmitted, the readmitting event, prior event(s) and provider(s), substantive healthcare and clinical status for the patient, treatment dates, and/or any other desired information. Readmission alerts can be formatted and provided in accordance with their consumers' parameters. Example methods and embodiments may receive, process, store, compare, and otherwise use any of HL7 messages, CCDA information, clinical feeds, or any other type of electronic healthcare record. This information may be received from any number of different healthcare information sources and providers. With example networks and methods, readmitting providers or other consumers of readmission notifications can know exactly when a patient is readmitted and adjust the healthcare response accordingly.

20 Claims, 3 Drawing Sheets

(56) References Cited

U.S. PATENT DOCUMENTS

| | | | |
|---|---|---|---|
| 8,185,408 B2 | 5/2012 | Baldwin, Jr. et al. |
| 8,489,423 B2 | 7/2013 | Hasan et al. |
| 8,528,056 B2 | 9/2013 | Robbins et al. |
| 8,527,295 B2 | 11/2013 | D'Ambrosia |
| 2005/0071194 A1 | 3/2005 | Bormann et al. |
| 2005/0203771 A1 | 9/2005 | Achan |
| 2005/0208941 A1 | 9/2005 | Ordille et al. |
| 2006/0178910 A1 | 8/2006 | Eisenberger et al. |
| 2008/0046286 A1 | 2/2008 | Halsted |
| 2008/0109447 A1 | 5/2008 | Mathur |
| 2008/0306759 A1 | 12/2008 | Ilkin et al. |
| 2009/0037020 A1 | 2/2009 | Brown |
| 2009/0222283 A1 | 9/2009 | Lassetter et al. |
| 2010/0076783 A1 | 3/2010 | Mathur |
| 2010/0082370 A1 | 4/2010 | Frederick et al. |
| 2010/0223073 A1 | 9/2010 | Nearman et al. |
| 2011/0112873 A1 | 5/2011 | Allen et al. |
| 2011/0119088 A1 | 5/2011 | Gunn |
| 2011/0178820 A1 | 7/2011 | Soni et al. |
| 2011/0258001 A1 | 10/2011 | Green, III et al. |
| 2011/0264467 A1 | 10/2011 | Green, III et al. |
| 2011/0270630 A1 | 11/2011 | Green, III et al. |
| 2011/0320469 A1 | 12/2011 | Canessa et al. |
| 2012/0101849 A1 | 4/2012 | Mathur et al. |
| 2012/0102502 A1 | 4/2012 | Mathur et al. |
| 2012/0108917 A1 | 5/2012 | Libbus et al. |
| 2012/0215560 A1 | 8/2012 | Ofek et al. |
| 2012/0246102 A1 | 9/2012 | Sudharsan |
| 2012/0239824 A1 | 10/2012 | Nguyen et al. |
| 2012/0253835 A1 | 10/2012 | Tracy et al. |
| 2012/0239420 A1 | 11/2012 | Stapelfeldt et al. |
| 2013/0085765 A1 | 4/2013 | Tuchinda et al. |
| 2013/0197929 A1 | 4/2013 | Vanderveen et al. |
| 2013/0197940 A1 | 8/2013 | Garber |
| 2013/0282394 A1 | 10/2013 | Baldwin et al. |
| 2013/0297328 A1 | 11/2013 | Johnson et al. |
| 2013/0325505 A1 | 12/2013 | Vengco |
| 2013/0345448 A1 | 12/2013 | Potter et al. |
| 2013/0346109 A1 | 12/2013 | Gunn |
| 2014/0136223 A1 | 5/2014 | Phillips |
| 2014/0278483 A1 | 9/2014 | Antony et al. |
| 2014/0278537 A1 | 9/2014 | Antony et al. |
| 2015/0193583 A1* | 7/2015 | McNair ................ G16H 50/20 705/2 |
| 2015/0242568 A1 | 8/2015 | Antony et al. |
| 2015/0242569 A1 | 8/2015 | Antony et al. |
| 2015/0242574 A1 | 8/2015 | Antony et al. |
| 2015/0310176 A1* | 10/2015 | Chen .................... G06F 19/327 705/2 |

OTHER PUBLICATIONS

Erica Galvez, HIE Bright Spots: How ADT Messages Support Care Coordination—Part II, Health IT Buzz, Mar. 26, 2013.

Improving Hospital Transitions and Care Coordination Using Automated Admission, Discharge and Transfer Alerts, Office of the National Coordinator for Health IT, May 2013.

ADT Alerts for Reducing ED Admissions, Indiana Health Information Exchange, 2013.

Curt Sellke, Related posts tagged with adt—Using ADTs as a starting point for valuable insights into accountable care delivery & Do you know where your patients are? (Parts I-III), Indiana Health Information Exchange, Mar. 13-Apr. 10, 2013 (available at http://www.ihie.org/listtag/adt).

Curt Sellke, Statewide Health Information Exchange Provides Daily Alerts About Emergency Department and Inpatient Visits, Helping Health Plans and Accountable Care Organizations Reduce Utilization and Costs, AHRQ Innovations Exchange, Jan. 29, 2014.

ALERT® Admission Discharge and Transfer (ADT), ALERT Life Sciences Computing, accessed Mar. 28, 2014 from http://www.alert-online.com/adt.

Functionalities, ALERT Life Sciences Computing, accessed Mar. 28, 2014 from http://www.alert-online.com/functionalities.

Chesapeake Regional Information System for our Patients, "The CRISP Response to the Request for Application for a Consumer-Centric Health Information Exchange for Maryland," Jun. 12, 2009 (available at http://mhcc.dhmh.maryland.gov/hit/hie/Documents/CRISP.pdf).

Chesapeake Regional Information System for our Patients, "CRISP Encounter Notification System," Dec. 27, 2013 (available at http://crisphealth.org/CRISP-HIE-SERVICES/Encounter-Notification-System-ENS).

Greg Goth, Event Notification Becoming Integral to HIEs, HealthData Management, Mar. 7, 2014.

Coastal Connect Health Information Exchange (CCHIE): Cutting through the clutter for care management, Medicity, accessed Mar. 26, 2014 from http://na-sj02.marketo.com/rs/aetnainc/images/Medicity%20Notify-CCHIE_20140218.pdf.

HealthCollaborate™ Transitional Care Management Application, HealthBi, accessed Mar. 26, 2014 from http://www.healthbi.com/solution/.

How does MicroBloggingMD work?, MicroBloggingMD, accessed Mar. 26, 2014 from http://www.microbloggingmd.com/basics.aspx.

Jupiter Medical Center's Physicians Use Innovative Technology to Keep Up-To-Date on Patients' Care, MicroBloggingMD, accessed Mar. 26, 2014 from http://www.prweb.com/releases/2014/03/prweb11691346.htm.

"Event Detection: A Clinical Notification Service on a Health Information Exchange Platform," Thomas Moore et al., AMIA Annual Symposium Proc. 2012; 2012: 635-642.

Catalyze, HL7 201—The Admission, Discharge, Transfer (ADT) message, Feb. 25, 2014 (available at https://catalyze.io/learn/hl7-201-the-admission-discharge-transfer-adt-message).

Chesapeake Regional Information System for our Patients, "CRISP Encounter Notification System," Dec. 27, 2013 (available at https://crisphealth.org/CRISP-HIE-SERVICES/Encounter-Notification-System-ENS).

* cited by examiner

NETWORK-BASED SYSTEMS AND METHODS FOR PROVIDING READMISSION NOTIFICATIONS

BACKGROUND

Healthcare information, including patient medical records and activities, facility encounters, insurance information, provider institutions, billing data, government healthcare support information, etc., across a large population can be aggregated in a Health Information Exchange (HIE) or similar database. For example, providers, insurers, and/or or governmental bodies may gather relevant healthcare information for all patients, providers, insurers, and other healthcare actors in HIEs. Because of the timing of healthcare information generation, the number of independent actors involved in healthcare administration, and privacy/proprietary aspects of healthcare information, HIEs may be largely computerized and operate with large degrees of autonomy and scalability to communicate amongst several independent users. HIEs may further employ healthcare information standards that permit reliable and secure exchange of healthcare information for millions of patients and users. An example of a related art HIE may be Maryland's CRISP network and associated Master Patient Index (MPI).

Figure 1:
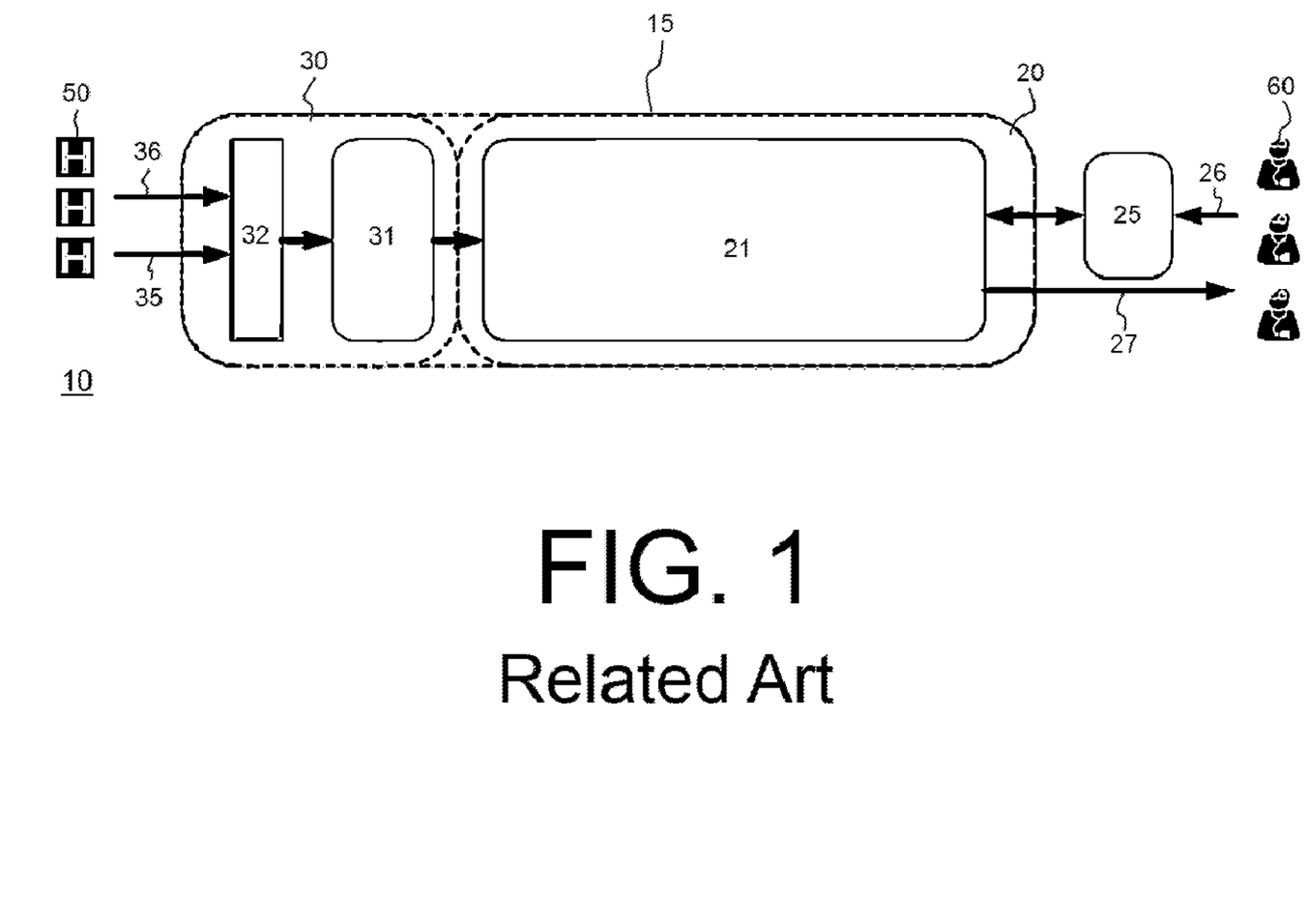
FIG. 1 is an illustration of a related art health information exchange system.

FIG. 1 is an illustration of a related health information exchange system 10. As shown in FIG. 1, system 10 includes a HIE 15 having a healthcare information routing and demographic matching structure 30, healthcare information database 21, and a healthcare information logic structure 20. Healthcare information routing and demographics matching structure 30 may be a digitized or computer-based system that facilitates entry, gathering, and organization of healthcare information from one or more providers 50.

For example, providers 50 may be emergency rooms, outpatient clinics, urgent care offices, pharmacies, laboratories, assisted living facilities, visiting nurse networks, etc. Providers 50 are conventionally the only source of healthcare information for HIE 15, acquired via healthcare information routing and demographics matching structure 30. For example, a provider 50 may provide clinical feeds 36, patient Admit-Discharge-Transfer (ADT) messages 35 in a known HL7 standard format, and/or any other healthcare information to healthcare information routing and demographics matching structure 30. The healthcare information, including content from clinical feeds 36 and ADT messages 35, may include many different types of relevant healthcare information, like patient biographical information, clinical treatment information, medical history, insurance information, provider activities, lab results, charges for services, emergency contacts, next of kin, etc. as well as nonclinical data like administrative codes, provider system IDS, etc. that typically reflect healthcare information on a per patient and/or per transaction basis. Particularly, ADT messages 35 may be generated and transmitted any time a patient has an encounter with a hospital 50, such as an admittance, discharge, transfer, to/from/within a hospital, and ADT messages 35 include this encounter information.

As shown in FIG. 1, healthcare information routing and demographics matching structure 30 may include an interface or router 32 that receives clinical feeds 36 and/or ADT messages 35 from hospitals 50. The router 32 may process or otherwise prepare data for entry into a database 21 and associated master patient index 31, which matches patient identifying information with content of database 21 to reconcile patient identity within health information exchange 15.

Conventionally, while only healthcare providers 50 deliver healthcare information to HIE 15, subscribing entities 60 may access healthcare information stored in database 21 of HIE 15. The healthcare information may be indexed by master patient index 31 and accessed through healthcare information logic structure 20 in health information exchange 15 that is interfaced with healthcare information routing and demographics matching structure 30. Subscribers 60 may be, for example, physicians needing comprehensive healthcare information regarding patients who present at urgent care or offices.

Two mechanisms may be provided in system 10 to provide information to subscribers 60. In one instance, subscribers 60 can login or otherwise access healthcare information logic structure 20 through a query portal 25. Subscribers 60 can enter queries 26 into portal 25, which is interfaced with healthcare information logic structure 20. Logic structure 20 may properly gather and/or associate data from database 21 with master patient index 31 based on the parameters of query 26 and any access/information rules applicable to system 10. In another instance, subscribers 60 may be delivered direct notifications 27, such as via email or alert every time an ADT message 35 or other healthcare update occurs to a patient. As such, information flow through conventional HIE 15 is typically wholesale and in a single direction, from healthcare providers 50 to HIE 15, which serves as a clearinghouse and organizer for all healthcare information, and then to subscribers 60.

SUMMARY

Example methods and embodiments manage healthcare information in computer-based networks between healthcare information sources. Example systems and methods are configured to receive healthcare information generated by healthcare information technology in response to patients presenting for treatment. Using this healthcare information electronically received, a computer processor can quickly determine when a piece of healthcare information indicates that a patient is being readmitted for treatment. Only when a readmission is identified, potentially among millions of pieces of healthcare information across several different providers and patients, the computer processor causes a readmission notification to be generated for the readmitting provider. The readmission notification can include any information about the patient and readmission—including patient identification, prior admissions and admitting provider(s), treated conditions, etc.—and may be provided on a schedule or in real time with the readmission. Readmission alerts can be customized based on the type of readmitting facility, parameters or limitations—such as timing or format—requested by the healthcare provider, default rulesets, timeframes between readmission and prior treatment, etc.

Example methods and embodiments work with a variety of different types of healthcare information, being configured to receive and process HL7 messages, CCDA information, clinical feeds, and several types of electronic provider output when treating patients. Example methods and embodiments can further work with any number of different healthcare information sources and providers, generating readmission alerts regardless of the triggering piece of healthcare information being generated by a patient's first encounter with a particular provider. Example methods and embodiments may process any of this healthcare information to identify patients and correctly associate the patient with a readmission event. In this way, readmitting providers or other consumers of readmission notifications may be notified only when making a readmission within particularly critical parameters and not receive multiple pieces of feedback for all healthcare information provided.

BRIEF DESCRIPTIONS OF THE DRAWINGS

Example embodiments will become more apparent by describing, in detail, the attached drawings, wherein like elements are represented by like reference numerals, which are given by way of illustration only and thus do not limit the example embodiments herein.

DETAILED DESCRIPTION

This is a patent document, and general broad rules of construction should be applied when reading it. Everything described and shown in this document is an example of subject matter falling within the scope of the claims, appended below. Any specific structural and functional details disclosed herein are merely for purposes of describing how to make and use example embodiments. Several different embodiments not specifically disclosed herein may fall within the claim scope; as such, the claims may be embodied in many alternate forms and should not be construed as limited to only example embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes any and all combinations of one or more of the associated listed items.

It will be understood that when element(s) are referred to in relation to one another, such as being "connected," "coupled," "mated," "attached," or "fixed" to another element(s), the relationship can be direct or with other intervening elements. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.). Similarly, a term such as "connected" for communications purposes includes all variations of information exchange routes between two devices, including intermediary devices, networks, etc., connected wirelessly or not.

As used herein, the singular forms "a", "an," and "the" are intended to include both the singular and plural forms, unless the language explicitly indicates otherwise with terms like "only a single element." It will be further understood that the terms "comprises," "comprising," "includes," and/or "including," when used herein, specify the presence of stated features, values, steps, operations, elements, and/or components, but do not themselves preclude the presence or addition of one or more other features, values, steps, operations, elements, components, and/or groups thereof.

It should also be noted that the structures and operations discussed below may occur out of the order described and/or noted in the figures. For example, two operations and/or figures shown in succession may in fact be executed concurrently or may be executed in the reverse order, depending upon the functionality/acts involved. Similarly, individual operations within example methods described below may be executed repetitively, individually or sequentially, so as to provide looping or other series of operations. It should be presumed that any embodiment having features and functionality described below, in any workable combination, falls within the scope of example embodiments.

The following co-owned applications are incorporated by reference herein in their entireties: U.S. application Ser. No. 13/844,332 to Antony et al. filed Mar. 15, 2013; U.S. application Ser. No. 14/142,625 to Antony et al. filed Dec. 27, 2013; U.S. application Ser. No. 14/189,225 to Antony et al. filed Feb. 25, 2014; U.S. application Ser. No. 14/189,278 to Antony et al. filed Feb. 25, 2014; U.S. application Ser. No. 14/189,306 to Antony et al. filed Feb. 25, 2014; and U.S. application Ser. No. 14/445,562 to Antony et al. filed Jul. 29, 2014. Moreover, the example methods and embodiments of the incorporated documents are useable in whole and in part in addition to, or in replacement of, example systems and methods, including individual components, elements, structures, steps, connections, actions, data structures, functionalities, etc. thereof.

The inventors have recognized that existing healthcare notification systems do not have a method for accurately and consistently alerting relevant healthcare stakeholders, such as providers and payers, when patients, members, and/or citizen populations experience healthcare encounters, and, more particularly, important types of healthcare encounters. Existing systems may use only information from the provider—such as only information contained in an HL7 ADT message itself—to route an alert to the appropriate recipient; however, such data often contains errors because it is commonly recorded by hand and relies on the information a patient relays at registration, sometimes under duress at an emergency room. Further, patients often do not provide or know all relevant information or may give incorrect information to a provider. As such, the inventors have newly recognized that conventional HIEs may pass incomplete or erroneous information on to interested subscribing entities and/or may fail to pass relevant information at all, because routing itself may be based on bad healthcare information contents. In addition to being under-inclusive and of poor quality, the inventors have further recognized that existing systems may pass too many pieces of healthcare information directly to providers identified in the information, resulting in overwhelming volume and irrelevancy of information provided, particularly in light of the hundreds of patients under any providers' or insurers' care that may be consuming healthcare at any time. This may cause recipients to become fatigued by constant and/or low-value messaging, resulting in less useful information for care management realized by existing systems.

The inventors have further recognized that specific types of filtering of healthcare encounters may provide limited, yet high-quality alerts to interested parties. Further, other sources of patient and healthcare information may be possessed by healthcare providers, insurers, governments, and other bodies not immediately performing healthcare services and can also be used to filter messaging and/or improve message accuracy/completeness and proper routing. Related art systems may not fully take advantage of the types of healthcare information received as a discriminator to provide only clinically-relevant alerts or the synergy between different healthcare information sources and providers to so enhance information delivery. Moreover, related art systems may not be sufficiently configured to connect and receive information from several different healthcare information sources and different types of healthcare information. The below disclosure uniquely enable solutions to these and other problems recognized by the inventors in computerized healthcare information networks handling huge amounts of healthcare data.

The present invention is computer networks, software, and/or hardware that receive healthcare information and selectively notify based on such receipt. The present invention is not—and the inventors and applicant explicitly disclaim—scope over a bare transitory signal or an abstract idea per se; while transitory signals and general concepts of arranging human behavior, comparing information and using rulesets based thereon, and categorizing information are useable with or in the present invention, the present invention is limited to particular implementations of those signals and concepts in connection with or to improve existing healthcare computerized information technology. In contrast to the present invention, the few example embodiments and example methods discussed below illustrate just a subset of the variety of different configurations that can be used as and/or in connection with the present invention.

Example Embodiments

Figure 2:
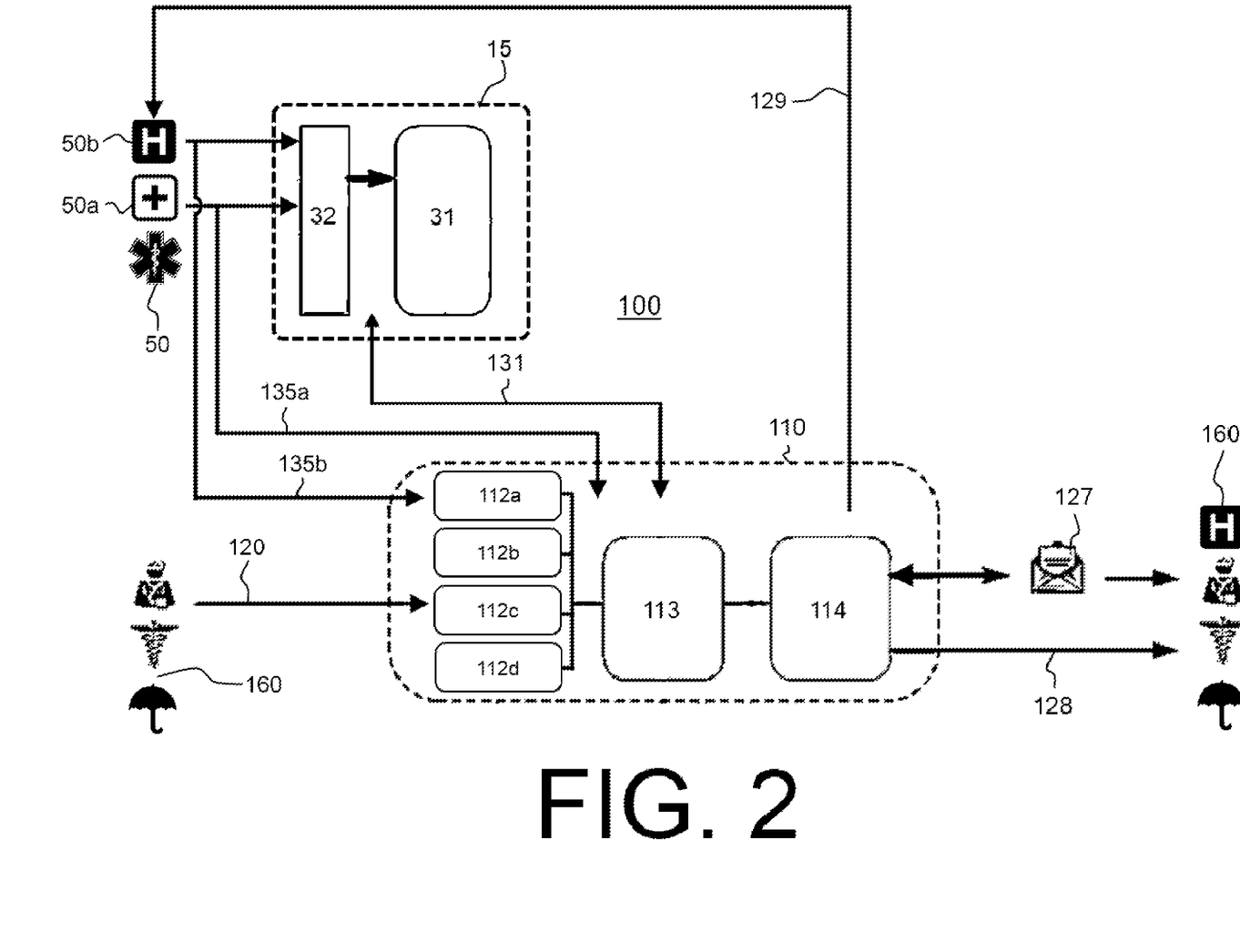
FIG. 2 is an illustration of an example embodiment healthcare notification system.

FIG. 2 is a diagram of an example embodiment healthcare notification system 100 that can be physically and logically configured through proper hardware infrastructure and/or software programming to provide targeted healthcare notifications and/or execute example methods of providing healthcare information. As shown in FIG. 2, example embodiment healthcare notification cluster 110 may be connected to a source of healthcare information, like a health information exchange (HIE) 15 and/or a healthcare provider 50 in example embodiment system 100. Healthcare notification cluster 110 and the source may be co-located or remote, and may be connected via a dedicated connection or bus in a same setting or over great distances through potentially shared networks such as VPNs, WANs, LANs, or the Internet, including TCP/IP and email exchanges.

Although example embodiment healthcare notification system 100 includes HIE 15 and/or actual providers 50 as healthcare information sources, it is understood that other types of sources for healthcare information are useable with example embodiments and methods. For example, a healthcare provider network system or other database having different data and interface configuration may be used in place of HIE 15. Still further, HIE 15 could be fully contained within healthcare notification cluster 110 to provide a centralized system for receiving, storing, processing, and/or delivering desired healthcare information to various subscribing providers 160. HIE 15 and providers 50, like a hospital or specialist clinic, may be equally be remote and operated by a distinct actor, such as a private corporation or state-operated database independent from cluster 110.

As shown in FIG. 2, healthcare notification cluster 110 is configured to receive subscriber information including subscriber parameters 120 from subscribing providers 160. Example embodiment healthcare notification system 100 is useable with a wide variety of subscribing entities 160 including both healthcare providers and other types of entities, including primary care physicians, specialists, insurance providers, hospitals, labs, clinics, home healthcare providers, government entities, researchers, etc. Subscribers 160 may really be any party who wants—or may be able to provide unique services with—specific healthcare information and notifications.

Subscriber parameters 120 define at least some services and/or actions to be provided by example embodiment system 100. For example, subscriber parameters 120 may include a roster of patient information—including patient name(s), hospital identifier, member ID, home address, city, state, zip code, date of birth, gender, ssn, phone numbers, membership status, family members, email addresses, etc. and/or portions thereof—identifying patients relevant to subscribers 160. For example, patient information submitted in parameters 120 may be associated with patients under the care of a primary care physician subscriber, covered by an insurance company subscriber, and/or under the jurisdiction of a governmental subscriber. Other subscriber information may also be transmitted separately and/or as a part of subscriber parameters 120, including subscriber name, type, service level, enterprise or tax identification numbers, delivery preferences, etc. described in greater detail below.

Subscriber parameters 120 may be input and/or updated into healthcare notification cluster 110 through a subscriber login interface, manually from delivered subscriber parameters 120 (such as from a spreadsheet via email), and/or automatically generated in cluster 110 based on a ruleset. For example, each subscribing provider 160 may provide subscriber parameters 120 to healthcare notification cluster 110 through any type of communication possible within a computer-processor-based network, including email, direct connection, manual input, etc. Subscribing providers 160 may provide multiple subscriber parameters 120 at signup and/or modify existing subscriber parameters 120, as their patients and needs and desires for healthcare information change.

Healthcare notification cluster 110 may include an input structure 112 to receive, process, and update/store information from subscriber parameters 120 in accordance with a transmission method used in example embodiment cluster 110. Input structure 112 may be, for example, a module or subroutine within healthcare notification cluster 110, a dedicated server with independent processing capability, and/or a common processor and database in notification cluster 110, depending on the configuration of healthcare notification cluster 110. In example embodiment healthcare notification cluster 110 of FIG. 2, several input structures 112a-d can be used, each with storage capability. Input structures 112a-d may be panels individualized to each subscriber 160; that is, each subscriber 160 may have a one-to-one assigned input structure 112x that stores subscription information, including subscriber parameters 120, only for the one assigned subscriber.

Subscriber parameters 120 stored by input structure 112 may include any kind of subscription information. As discussed above, subscriber parameters 120 may set out a roster of responsive client identifications. Subscriber parameters 120 may further delimit a variety of circumstances for which subscribing providers 160 desire healthcare information, including any combination of events or message types based on which to create notifications, frequency of notifications, delivery format, type preferences, etc. For example, parameters 120 may include a limiting set of events or circumstances for which subscribing providers 160 desire healthcare information. Further, subscriber parameters 120 may include healthcare information formatting, delivery options, analysis, and/or enhancement selections.

Example embodiment healthcare notification cluster 110 is interfaced with a healthcare information source. For example, cluster 110 may include an HIE interface 131 that is configured to communicate with healthcare information sources, such as MPI 31, HIE interface 32, and/or entire HIE 15. Or, for example, cluster 110 may include a provider connection 135 that is configured to communicate directly with providers 50, like hospitals, doctor's offices, pharmacies, home healthcare workers, clinics, etc. Thus, cluster 110, via logic core 113 and/or a separate interface, may recognize and understand how to retrieve, read, and/or write specific data structures or information association regimes present within MPI 31, such as client IDs, patient-identifying information, relationships among entries and records, etc., stored in MPI 31.

Similarly, cluster 110, via logic core 113 and/or a separate interface, may recognize and understand how to receive and process healthcare information directly from providers 50 transmitted via direct provider interface 132. As a specific example of healthcare information from a provider 50, a hospital 50 may generate a summary of care document(s) during a patient encounter, like a discharge. The summary of care document may include healthcare information like patient biographical information, insurance information, treatment information, health history, etc., and may be in a standard electronic health record format, like a Consolidated Clinical Document Architecture (CCDA) message. The CCDA message may be sent directly over interface 132, such as via email using Direct protocol or other HIPAA-compliant secure communications.

Of course, other information types can be transferred over interface 135, such as clinical feed information and/or all HL7 messages from providers 50, which may be thousands or more of HL7 messages per day including ADT-type messages. Cluster 110, via logic core 113, an intake module of direct provider interface 132, and/or another interface can recognize and be able to process information in specific data formats and information relationships sent directly from providers 50, including CCDA summary of care documents and ADT messages, for example.

Although interfaces 131 and 135 are shown as separate in FIG. 2, this is only to describe functionalities. It is understood that, with any interface, direct communications from providers 50 to cluster 110 may be achieved. For example, interface 131 may be directly accessed by providers 50 in HIE 15, such that provider 50 may still directly provide information to cluster 110. Similarly, HIE 15 may itself be wholly or part of a provider 50, and/or wholly or part of cluster 110, such that providers 50 and/or cluster 110 may assume all functionalities of HIE 15, either shared or exclusively. In these ways, a direct provider interface 135 may be a single interface 131.

Healthcare notification cluster 110 in example embodiment system 100 may also include a notification engine 114 controlled by logic core 113. As with each component of cluster 114, notification engine may be a functionality wholly programmed in logic core 113 or can be a separate module or even a remote server with its own processor and persistent and transient memory that is programmed or configured hardware to perform notification functionality in accordance with example methods or otherwise.

In view of this flexibility of cluster 110 and the necessarily computerized nature of HIEs and example embodiments and methods, as used herein, "logic core" and "(computer) processor" in cluster 110 are defined to include any and all computer hardware processor(s)—whether divided, remote, co-located, and/or singular—and any associated bus and memory that are configured through programming and/or hardware and structural connections to electronically communicate with healthcare IT systems including HIEs, intake and patient processing systems at healthcare providers, insurers' computer systems, and subscribers' computers. Given the thousands, if not millions, of healthcare encounters and transactions and associated pieces of healthcare information received daily and processed in example methods—including filtering, formatting, selective forwarding, and analysis of such data based on subscriber parameters and/or other stored data—it is further understood that logic core 113 must be sufficiently large and powerful to process such data and execute example methods in "real time"—i.e., instantaneous as perceived by a human user or at least within the timeframe of the task or action that triggers example methods.

Notification engine 114 can prepare healthcare notifications from data anywhere in system 100, such as data derived from ADT messages via interface 135, MPI 31, healthcare analysis stored in cluster 110, and/or any other healthcare information. Notification engine 114 may further provide the prepared information in a subscriber notification. Healthcare notifications may be delivered to subscribing providers 160 through a report 127 sent via email, over a direct or secure network, through the Direct standard, in HL7 format, via Internet services, or even hard copy, based on profile information 120 or other rules. Based on the method used, return receipt or other feedback on delivery of report 127 may be received in cluster 110. For example, under Direct protocols, a Direct email message sent to a subscriber 160 containing responsive information from a CCDA received and matched with the subscriber by cluster 110. The receiving subscriber 160 may send a return receipt, such as a Message Disposition Notification, back to the secure Direct email address of cluster 110 acknowledging receipt. Cluster 110 may store such acknowledgement and/or make it available to the original provider 50 that generated the CCDA that ultimately resulted in the notification 127 being sent.

Healthcare notifications may be structured as narratives, tables, spreadsheets, existing encounter formats, etc. by notification engine 114. For example, notification engine 114 may compile and email out a report of all healthcare information received, filtered, and/or formatted by logic core 113. Healthcare notifications may also be prepared and stored with notification engine 114 and provided to subscribing providers 160 only upon their access 128 to healthcare notification cluster 110; a reminder of a new healthcare notification may still be provided in this instance. Still further, a subscribing provider 160 may receive and/or acknowledge notifications via the Direct standard in real-time from notification engine 114, which may store or further process such acknowledgements.

Notification engine 114 may further include a reverse notification interface 129 to provide information back to healthcare providers 50. Although interfaces 129, 131, and 135 are shown as separate structures/connections, it is understood that these interfaces may be shared or even further divided. Interfaces 129, 131, and 135 are shown as separate to illustrate the ability for different types of information and functionalities to be provided among different actors. For example, cluster 110 may acknowledge receipt of healthcare information via return Direct email over interface 135 to providers 50, and equally over reverse notification interface 129.

Reverse notification interface 129 may permit more rigorous information, such as the results of filtering, correction, compiling, and/or other functions provided by cluster 110, to be provided back to providers 50 from notification engine 114. For example, notification engine 114 may provide the same notifications that subscribers 160 receive back to the healthcare provider 50 that provided the original healthcare message that caused the notification to be generated.

Further, notification engine 114 may provide specialized information generated through example methods back to providers 50, including subscriber information, potentially in response to any number of specialized triggers and in any desired format or timeframe. For example, notification engine 114 may provide an indicator to a second provider 50b that submits healthcare information about a patient over interface 135b to cluster 110; the indicator may show that the same patient was discharged within a recent timeframe from first, distinct provider 50a based on a prior-received and stored piece of healthcare information over interface 135a.

Reverse notification interface 129 may be utilized to return information to providers 50 regardless of subscriber status. That is, providers 50 themselves could also be subscribers 160, in which case reverse notification interface may simply be interface(s) 127 and/or 128. Or no subscribers 160 could exist, and providers 50 may not subscribe to cluster 110, but reverse notification interface 129 may nonetheless deliver information to healthcare provider 50 based on specific types of healthcare information generated and transmitted by provider 50.

As referenced above in connection with the flexibility of cluster 110, logic core 113, any communications interface 131, 135, 127, 128, 129, etc. may be a central routine executed on specifically-configured processor networked to an electronic network, individual and distinct servers and routers with independent storage and processors potentially operating on diverse operating protocols, or any other hardware capable of performing electronic communication. Interfaces in example embodiment system 100 can be over the Internet, including standard communications protocols such as TCP/IP or email, and/or through a programmed application configured to interact with and exchange data in dedicated network or intranet. Servers within example embodiment system 100 may include, for example, conventional domain and/or security and encryption protocols for access and authentication as well as processing capacities to retrieve, deliver, and/or format data for use within example embodiment system 100.

Similarly, although networked elements of example embodiment system 100 are shown in FIG. 2 as individual components with specific groupings and subcomponents, it is understood that these elements may be co-located in a single device having adequately differentiated data storage and/or file systems and processing configurations. Alternatively, the elements shown in FIG. 2 may be remote and plural, with functionality shared across several pieces of hardware, each communicatively connected at adequate speeds to provide necessary data transfer and analysis, if, for example, more resources or better logistics are available in distinct locations. Given the variety of example functions described herein, healthcare notification cluster 110 may be structured in a variety of ways to provide desired functionality. Other divisions and/or omissions of structures and functionalities 112, 113, and 114 among any number of separate modules, processors, servers are useable with example embodiment system 100, including execution on a single machine or among distant, exclusive servers and processors.

Although the example embodiment system 100 of FIG. 2 is a computer-based system that can be configured with and execute example methods, it is understood that example methods are useable with other network configurations, and system 100 is useable with other methods of healthcare delivery.

Example Methods

Figure 3:
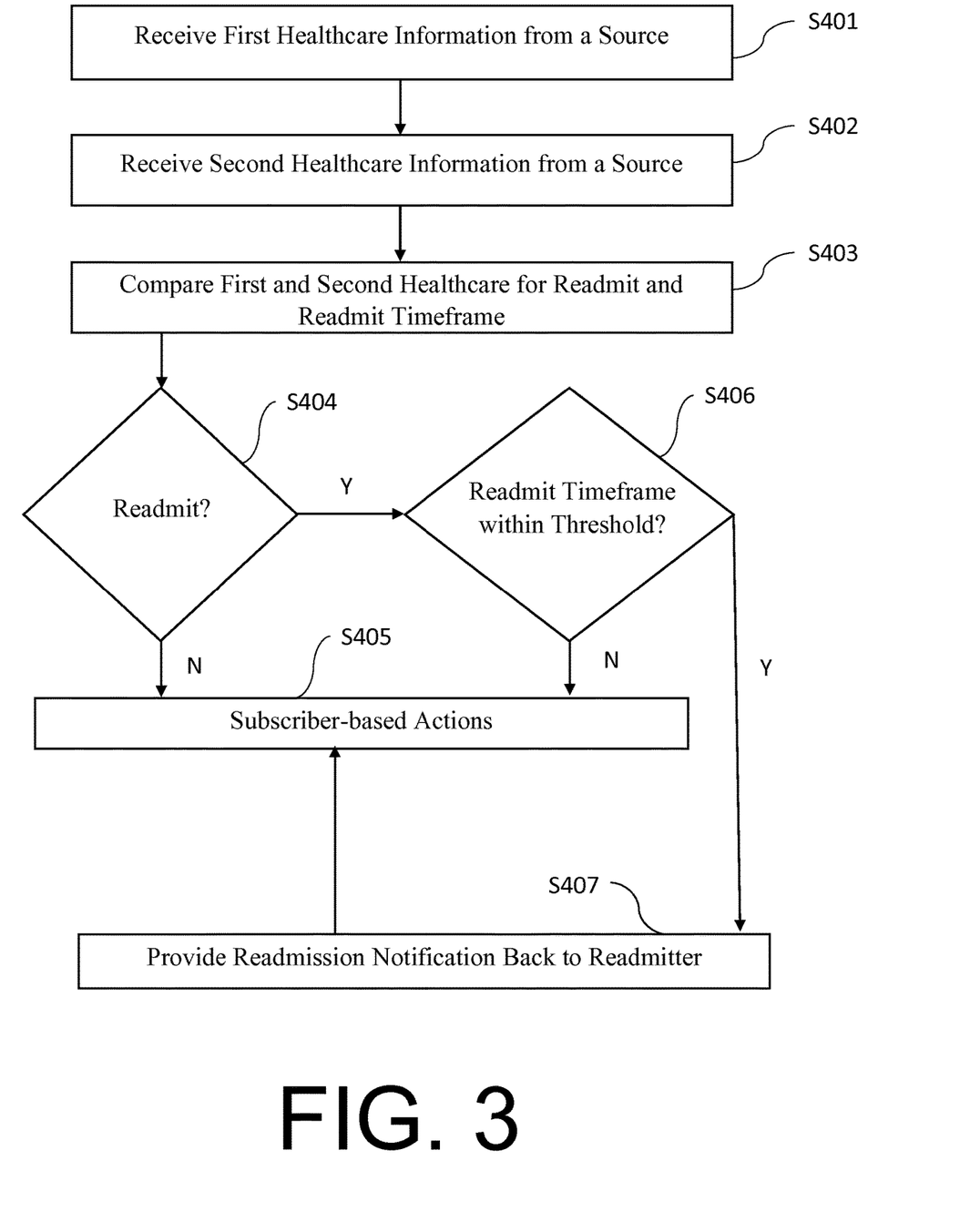
FIG. 3 is a flowchart of an example method of providing readmission notifications.

Based on healthcare information received from a healthcare information source and potentially subscriber parameters received from a subscriber, a computerized healthcare notification engine can collect, compile, enhance, analyze, and/or provide specific and well-tailored healthcare information back to a healthcare information source. In the context of FIG. 2, healthcare notification cluster 110 includes a logic core 113 interfaced with and/or controlling operation of HIE 15 as well as interfaced directly with providers 50. Logic core 113 may coordinate actions of example methods, including healthcare message processing and analysis, retrieval of healthcare information, delivering healthcare information in accordance with subscriber parameters, delivering healthcare information back to healthcare providers based on types of information received, enhancement of MPI 31, and/or several other functions discussed further herein. FIG. 3 is a flow chart illustrating an example method of healthcare information and notification processing. Using an example network 100 from FIG. 2, logic core 113 may provide healthcare message processing in the example method of FIG. 3. As such, while an example method is described in connection with FIG. 3, it is understood that structures and reference characters executing the same may refer back to FIG. 2.

In S401, healthcare information regarding a patient is received from a first source 50a—like a hospital, HIE, doctors office, pharmacy, etc. The receipt in S401 may be similar to receipt in methods described in the incorporated documents above. For example, in S401, cluster 110 may receive an admit-type ADT message in HL7 format from an admitting emergency room 50a directly via interface 135a. Or, for example, in S401, cluster 110 may receive a CCDA format document from a specialty clinic 50a through HIE 15, indicating discharge of a patient from the clinic following a specialty procedure.

As part of the receiving in S401, logic core 113 may store the healthcare information in connection with the treated patient in cluster 110 and/or HIE 15. For example, a programmed processor capable of communicating on a same standard as the healthcare source and programmed to parse the format of the received healthcare information may extract patient identification, treatment, and/or discharge conditions from the healthcare information and write the extracted data in association with the patient in a memory in cluster 110 or in MPI 31 for example. The receiving in S401 may, like any other action in example methods, occur repeatedly, potentially several or thousands of times a day, given the level of healthcare information typically passed through computerized healthcare networks.

In S402, another receipt of healthcare information occurs after the receipt in S401. The receiving in S402 may be substantially similar to that in S401, but at least differs in time of receipt. For example, the healthcare information received in S402 may concern a same patient as that received in S401, but with different treatment information and administrative actions. Or, for example, a hospital 50b may generate an admission type ADT and transmit it for reception in S402, following a prior discharge-type ADT message received for the patient in S401. Receipt in S401 and S402 may involve permanent or transient electronic storage of the raw or processed information received in S401 and S402.

In S403, the first and second healthcare information received in S401 and S402 are compared to determine whether a same patient is being readmitted for healthcare treatment, and a timeframe of such readmission. Readmissions within a short timeframe (within several months) typically reflect inefficient healthcare results, whether it be due to particularly recalcitrant or chronic disease states, poor quality of clinical healthcare delivery, and/or noncompliant or malingering patients. Further, under insurer and government healthcare-payer rules, providers may be penalized for readmissions for a same condition or within a sub-optimal timeframe. The inventors have recognized that healthcare providers are highly benefited by identifying readmissions as well as patients that represent a readmission risk based on previous readmissions, owing to these negative consequences of readmission.

There are several ways to determine a readmission in S403. For example, the second received healthcare may be compared against all previous received healthcare, whether in a local cluster or stored in a remote database like an MPI, to determine if a same patient has been subject to a recent treatment. The same comparison may be isolated to comparing only information responsive to a same patient or based on treatment condition, if included in the healthcare information. As an example of a specific algorithm, a patient identified in the second healthcare information may be searched against all previously-generated first information for the same patient, and discharge or other treatment-completion-type information can be identified within the matching first information, to verify that the second information represents a readmission for a same patient that should trigger a readmission notification or potentially return a "readmission not found" type message.

As an even further specific example of S403, the first information received in S401 may include an HL7 ADT message indicating a discharge from a first provider 50*a* (FIG. 2) at a first date, and the second information received in S402 may include an HL7 ADT message indicating an admission from a second provider 50*b* (FIG. 2) at a second date shortly after a first date for a same patient. A processor in cluster 110 (FIG. 2) may, in real-time, determine that these two ADT messages represent a readmission of the patient in S403. Similar analyses may be completed for CCDA messages, clinical feeds, and other information electronically received from healthcare providers indicating patient treatment. HL7 ADT messages, being standard, relatively short administrative messages generated by a healthcare provider's IT system in response to an actual patient healthcare event, may be particularly beneficial in permitting accurate and fast determination of readmission by identifying a discharge and later admission for a same patient through simple, unambiguous fields.

In S403, an amount of time between readmission for a particular patient is also determined. For example, logic core 110 (FIG. 2) may compare times/dates of receipt among the first and second information for the patient. Or, for example, the first and second healthcare may be processed in order to determine timeframe, such as by extracting a date of admission and/or discharge in the information. Determination of timeframe itself, alone or in combination with other information, may aid in the identification of admission in S403. For example, extremely short timeframes on the order of minutes or hours between received healthcare information for a patient may be a result of redundant or spurious data entry and may not indicate readmission.

In S401-S403, the received healthcare information can be corrected, enhanced, and/or processed in any other manner to potentially increase readmission identification accuracy. For example, logic core 113 may further process received healthcare information to discard messages or portions of information containing duplicate, incorrect, or low-value contents. For example, a provider 50 may generate an ADT message 35 for an internal transfer that has no meaning outside the provider facilities, or a received healthcare information may include typographical errors in a patient's information or an impossible/redundant administrative status change, such as duplicative admittances for the same patient and facility. A computer processor appropriately interfaced and programmed can so analyze received electronic healthcare information for such errors, for example, under internal rules for discarding impossible types of actions, clear typographical errors, or unusable data in S401-S403.

Similarly, in S401-S403, received healthcare information can be enhanced with additional information not necessarily from the originating source. For example, received healthcare information in S401-S403 may be corrected and supplemented with information in MPI 31 and/or subscriber parameters 120 to ensure a proper patient is identified, spurious information is removed, a complete record of the patient is generated, etc. Several example methods in the incorporated documents and otherwise can be used to improve or add additional information to any type of received healthcare information, from sources as diverse as subscriber parameters, information stored in a health information exchange, and data stored in a cluster executing example methods. Potentially-corrected records for each healthcare information receipt may thus be generated and further stored, locally in cluster 110 or remotely such as in MPI 31, for direct, accurate, and/or real-time comparison of all of a patient's healthcare information to determine a readmission in S403.

In S404 and S406, example methods selectively proceed depending on the results of the comparing in S403. In S404, if a readmission of a patient by the source providing the second healthcare information is determined, the method proceeds. Further, in S406, if the readmission has occurred within a threshold timeframe as determined in S403, the method proceeds. The threshold timeframe in S406 may be several different spans of time. For example, the threshold timeframe may be a previously-provided timeframe by the readmitting healthcare provider that generated the information indicating the readmission. Or, for example, the threshold timeframe may be a default that matches regulatory or legal penalties for readmissions, such as two months. Or, for example, the healthcare provider from which the readmission-indicating healthcare information is received may also be a subscriber (120), and the threshold may be set in accordance with subscriber parameters or other default rules for subscribers.

If in S404 and S406 a readmission for a same patient has occurred, and the readmission has occurred within the threshold timeframe, example methods proceed to S407, where the readmitting healthcare facility is alerted of the readmission. In S407 a readmission alert for the patient identified in S403 is compiled for transmission to the readmitting healthcare provider. The readmission alert may be any information indicating a readmission, and the alert may include information compiled from several sources. For example, in S407, logic core 113 may compile the triggering piece of healthcare information, such as an admission-type ADT message received from second provider 50*b*, a most recent discharge and/or treatment of the patient, such as a discharge-type ADT message on file from first provider 50*a*, and an amount of time through readmission, such as a span of time between receipt of the ADT messages from providers 50*a* and 50*b*. Any or all of this information may be provided back to the determined readmitting healthcare provider. Or for example, a readmission alert may be an extremely short and simple flag with patient identifier electronically transmitted in potentially only a dozen or so characters.

Logic core 113 may format and time any readmission alert being provided back to the readmitting healthcare provider in accordance with any parameter. For example, healthcare providers 50 may provide readmission notification limitations or parameters to cluster 110 to control the readmission alert generation process. Such limitations may define situations where a readmission notification is not desired—for example, limitations may list patients for whom no readmission alert should ever be generated, may request readmission alerts only if it is known that the prior admission was for a same condition or at a particular provider, and/or compel readmission notifications even outside of typical timelines for certain classes of patients based on insurance, age, condition, etc. The parameters may further define a special formatting for particular types of encounters and/or patients, additional information to be added to the notifications, delivery format or frequency requirements, etc. Such limitations may be provided by the readmitting provider in any manner, including as subscriber parameters 120 if the provider 50 is also a subscriber 160, with the triggering healthcare information, as a separate piece of information transmitted to a healthcare exchange 15, etc. Of course, timeframe information for identifying a readmission within a particular timeframe in S403 may be provided alongside these limitations or separately.

In S407, the readmission notification, potentially with compiled, formatted, and/or enhanced information about the patient or readmission in general is provided back to the readmitting healthcare provider, potentially in real-time with the readmission. For example, the readmission notification could identify the patient by name or patient ID, give a number of discharges in connection with specific conditions, list a most recent discharge or other event illustrating the readmit, show prior healthcare provider(s), list known conditions, include full biographical information of the readmitted patient acquired from subscriber parameters, etc. In S407 logic core 113 may control notification engine 114 to generate readmission notifications only at appropriate times and manners based upon provider preferences or limitations previously received or defaulted based on provider type. The readmission notification can be provided through reverse interface 129 to the readmitter, back through HIE 15, and/or back through any other electronic channel (129, 131, 135, and if the readmitting provider is a subscriber, 127 and 128) through which the readmitting provider can receive readmission notifications. The notifications may take the form of electronic messages, HL7 protocol messages sent to HL7-compatible healthcare provider IT, email messages, or provided upon login to cluster 110, similar to interface 127.

If the received second healthcare information does not indicate a readmission, or such readmission is not within a threshold timeframe, a readmission notification is not provided in S407. Of course, at any point in example methods, regardless of readmission status or readmission notifications provided to a readmitting healthcare provider, example methods may include providing subscriber-based services S405. Such subscriber-based services are further detailed in the incorporated documents. The subscriber-based services, even though shown separately, may nonetheless include information generated in S401-S404 and S406. For example, providers may query a notification cluster for subscription or readmission information in S405. The notification cluster may provider such information—including readmission information—back to the provider before, after, or during readmission notifying. In this way, a provider or any other requester may still receive readmission information for a patient even if a readmission notification is not generated in S407, such as where a readmission falls outside of a threshold timeframe, fails to meet a provider preference for notifications, or does not exist. For example, a provider 50 may request from cluster 100 readmission information for a patient, potentially along with ADT or other clinical information about the patient, via interface 131 or 135, and cluster 110 may return a "0" or "no readmission" for the patient via interface 129, or may return an admission history or count that may nonetheless exceed readmission thresholds in S405.

This paragraph offers an example of S401-S407 taken together. Hundreds of thousands of electronic messages, clinical feed data, ADTs, CCDAs, etc. in various formats including HL7 are received at cluster 110 for thousands of different patients from hundreds of different sources each day, including healthcare providers 50 and/or state-operated HIE 15. A programmed computer processor in cluster 110 processes each piece of this deluge of healthcare information, identifying and storing clinically-relevant information in correct association with each patient actually treated. Eventually, an admit-type ADT message in HL7 standard is received from a flagship hospital emergency room 50*b* for patient John Doe in cluster 110. In real-time, while the emergency room 50*b* is still processing patient John Doe for treatment, cluster 110 identifies a CCDA document that has been previously received from an unassociated specialty clinic 50*a* four weeks ago and stored in connection with patient John Doe. Based on cluster's earlier processing of the CCDA document from the clinic 50*a*, cluster 110 identifies that patient John Doe is now being readmitted within four weeks of a previous discharge. Based on processing of the earlier CCDA and the new ADT message, cluster 110 may verify that the readmission is real and even that the readmission is problematically associated with a same disease state. Because four weeks is within the default six-week timeframe threshold programmed in cluster 110, cluster 110 generates a readmission notification based on the ADT message from hospital emergency room 50*b*. Cluster 110 then provides the readmission notification to emergency room 50*b*, identifying a readmission within six weeks for patient John Doe. The readmission may be received for interface 129, via HIE 15, through a subscriber alert 128/127 or any other electronic method to enable the real-time notification of this example. The notification may further include information about the previous discharge from clinic 50*a*, other discharges for patient John Doe within a same of other timeframes, biographical or healthcare information for patient John Doe, and/or any other information or formatting potentially requested by emergency room 50*b*. Upon receipt of the readmission notification from cluster 110, hospital 50*b* knows that the patient John Doe has very recently presented for other healthcare treatment, potentially for a same or other high-risk condition, potentially before even providing healthcare to John Doe. Admission, diagnosis, and treatment decisions may thus be adjusted based on the accurate knowledge or a recent prior discharge and heightened risk of further readmissions. The readmission alert provided to hospital 50*b* is done while multitudinous other pieces of healthcare information received at cluster 110 do not generate such a notification, potentially because they are identified as spurious, regarding other patients, or not indicative of a readmission for patient John Doe.

It is understood that several aspects of the methods possible from the flowchart of FIG. 3 are optional and may occur only in specific conditions. For example, only S401-S405 may occur in the event of a non-readmission, such as when an admission flag from a healthcare provider 50 is received that does not correspond to a patient having prior-received information identifying a discharge for the patient. Or, for example, S400-S404, S406, and S407 may all occur when healthcare information is received that indicates a readmission based on prior-received information, but no subscriber identifies that patient for execution of subscriber-based actions. Several other action permutations are of course possible, including reversal or combination of decisions S404 and S406. As such, healthcare information sources may receive information about readmitting patients simply by transmitting an admission through example methods.

It is further understood that example methods may service any number of distinct providers 50 and/or HIEs 15, including entire community- or-jurisdiction-level populations with hundreds of providers and millions of patients. Example methods are necessarily computerized, and, indeed, the only way to compare all, numerous received pieces of electronic healthcare information in S403 for determination of readmission across any reasonable healthcare population is with a programmed and significantly-powered computer processor and memory. That is, there is no way to successfully determine and notify readmitting healthcare providers even in a modest-sized provider network or small municipality about every patient they are treating that is a readmit while filtering out all other information for non-readmissions without a specifically-programmed and interfaced processor and memory, let alone in real-time, let alone with readmission timeframe determination and filtering, let alone with healthcare information correction and enhancement, let alone in a large network with hundreds of independent healthcare providers or a large state, or let alone with additional subscriber notification methods. As such, the present invention is strictly computerized and significantly limited to implementations that are highly involved with, and improve the function of, computerized healthcare IT.

As with all healthcare information sharing among separate parties, appropriate safeguards—including encryption, encoding, and/or communications protocols like HL7 and Direct—may be placed on any interface and transmission in example embodiments and methods. It is understood that Direct and HL7 protocols are defined by their standard-setting bodies, explained at http://wiki.directproject.org/ and http://www.hl7.org/implement/standards, with current and future editions of these standards included in the terms "HL7" and "Direct." As an example of Direct protocol, "Applicability Statement for Secure Health Transport," version 1.2, Aug. 3, 2015 is incorporated herein in its entirety by reference. Similarly, because providers 50, HIEs 15, subscribers 160, cluster 110, and patients can all be distinct actors with independent owners and operators with distinct interests in healthcare information, appropriate consents and HIPAA-compliant releases may be secured or required from each independent party before any information exchanging or usage is executed in any example method.

Some example methods being described here and in the incorporated documents, it is understood that one or more example methods may be used in combination and/or repetitively to produce multiple options and functionalities for subscribers. Example methods may be performed by properly programming or hardware configuring notification networks to receive healthcare information and subscriber information and act in accordance with example methods. Similarly, example methods may be embodied on non-transitory computer-readable media that directly instruct computer processors to execute example methods and/or, through installation in persistent memory, configure general-purpose computers connected to subscribers and healthcare information sources into specific healthcare notification networks that execute example methods.

Example methods and embodiments thus being described, it will be appreciated by one skilled in the art that example embodiments may be varied through routine experimentation and without further inventive activity. For example, although compared healthcare information used to determine a readmission is shown as originating from two independent healthcare providers having it is understood that a readmission may be determined and alert issued from healthcare information all received from a same, commonly-controlled provider. Variations are not to be regarded as departure from the spirit and scope of the exemplary embodiments, and all such modifications as would be obvious to one skilled in the art are intended to be included within the scope of the following claims.

What is claimed is:

1. A method comprising:
   electronically receiving, with a notification system including a computer processor and memory networked with a plurality of distinct healthcare information sources, healthcare information in several different formats dependent on hardware and/or software used by a computer of the sources from the plurality of distinct healthcare information sources and including treatment details for patients at a first healthcare provider and a second healthcare provider;
   parsing, with the computer processor, the healthcare information for HL7 Admit-Discharge-Transfer (ADT) messages and storing patient-identifying information in a standardized format from the HL7 ADT messages in the memory;
   determining, with the computer processor, from the stored patient-identifying information, a readmission time for a patient by comparing a first HL7 ADT message indicating admission of the patient at the first healthcare provider against a second HL7 ADT message for the patient, wherein the readmission time is a difference in time between the first HL7 ADT message and the second HL7 ADT message;
   generating in real-time with receipt of the first HL7 ADT message, with the computer processor, a readmission notification for the patient and transmitting the notification to the first healthcare provider so that the first healthcare provider has immediate access to up-to-date patient information, wherein the generating is executed if,
      the readmission time is within a readmission time threshold stored in the memory, and
      the patient-identifying information indicates the first HL7 ADT message and the second HL7 ADT message identify a same patient.

2. The method of claim 1, further comprising:
   electronically receiving, from the first healthcare provider, parameters that control the format of the readmission notification and include the readmission time threshold, wherein the generating causes the readmission notification to be presented in accordance with the parameters.

3. The method of claim 1, wherein the healthcare information includes at least two thousand messages including a third HL7 ADT message indicating admission of the patient outside of the readmission time threshold, and wherein no generating is executed based on additional messages outside the threshold.

4. The method of claim 1, wherein the readmission time threshold is 6 weeks and not received at the notification system from the first healthcare provider.

5. The method of claim 1, wherein the second HL7 ADT message is generated by the second healthcare provider and indicates a discharge of the patient from the second healthcare provider, and wherein the first and the second healthcare provider are independent and lack common control and ownership from each other.

6. The method of claim 1, wherein the healthcare information is directly received and stored by the notification system from the healthcare providers.

7. The method of claim 1, wherein the second HL7 ADT message is a discharge-type ADT message for the patient generated within the readmission time threshold from the first HL7 ADT message.

8. The method of claim 1, further comprising:
receiving a plurality of subscriber parameters from a plurality of subscribers; and
enhancing the healthcare information with additional information about the patient, wherein the additional information is from the subscriber parameters, and wherein the receiving includes receiving the healthcare information as enhanced.

9. The method of claim 1, wherein the difference in time between the second HL7 ADT message and the first HL7 ADT message is an amount of time calculated by subtracting a discharge date extracted from the second HL7 ADT message from an admission date extracted from the first HL7 ADT message.

10. A method comprising:
storing information in a standardized format about a patient's condition from a first HL7 Admit-Discharge-Transfer (ADT) message in a network-based non-transitory storage device storing a collection of medical records;
providing remote access to a plurality of independently-operated healthcare providers over a network so any one of the providers can provide a plurality of pieces of healthcare information generated by the plurality of healthcare providers through a computer of a provider updating the information about the patient's condition, wherein the pieces of healthcare information include at least two thousand pieces of healthcare information generated in a day and are not in the standardized format and dependent on hardware and/or software used by the computer of the provider;
parsing, with a computer processor in the notification system, the plurality of pieces of healthcare information for HL7 ADT messages for the patient;
storing a second HL7 ADT message for the patient from the HL7 ADT messages for the patient in the standardized format in the notification system;
comparing, with the computer processor in the notification system, the first HL7 ADT message of the pieces of healthcare information against the second HL7 ADT message of the pieces of information to determine a discharge and a later admission of the patient and a readmission time for the patient that is a difference in time between the first HL7 ADT message and the second HL7 ADT message; and automatically generating and transmitting, with the computer processor in the notification system, to a computer of the healthcare provider that generated the second HL7 ADT message a readmission notification in real-time with the second HL7 ADT message being received, wherein the readmission notification identifies the readmission based on the comparing so the healthcare provider has immediate access to up-to-date patient information, wherein the generating and transmitting is executed if,
the readmission time for the patient is within a readmission time threshold stored in a memory.

11. The method of claim 10, wherein the first HL7 ADT message is a discharge-type ADT message, and wherein the second HL7 ADT message is an admit-type ADT message.

12. The method of claim 11, wherein the readmission notification identifies the patient and the discharge-type ADT message.

13. The method of claim 10, wherein the plurality of healthcare providers are distinctly located, owned, and controlled from each other and the computer processor, and wherein the plurality of healthcare providers are connected to a same health information exchange.

14. The method of claim 10, wherein the first HL7 ADT message and the second HL7 ADT message are generated by different healthcare providers that are independently operated from each other.

15. The method of claim 14, wherein the difference in time between the first HL7 ADT message and the second HL7 ADT message is an amount of time calculated by subtracting a discharge date extracted from the first HL7 ADT message from an admission date extracted from the second HL7 ADT message.

16. A notification system networked among several independent data feeds, the system comprising:
a first interface configured to read healthcare information in a first protocol from a first healthcare provider;
a second interface configured to read healthcare information in a second protocol from a second healthcare provider, wherein the first and the second protocols are different health record standards;
a third interface configured to instruct a computer at the second healthcare provider to display a readmission notification; and
a computer processor networked with the first and the second healthcare providers via the first, the second, and the third interfaces, wherein the computer processor is configured to,
electronically read a plurality of pieces of healthcare information generated by the first and the second healthcare providers, wherein the pieces of healthcare information include treatment details for patients at the healthcare providers and are in the first and the second protocols,
parse the healthcare information for HL7 ADT Admit-Discharge-Transfer (ADT) messages and store patient-identifying information in a standardized format from the HL7 ADT messages in a memory,
compare a first HL7 ADT message of the pieces of healthcare information indicating a discharge of a patient against a second HL7 ADT message of the pieces of healthcare information indicating a later admission of the patient to determine a readmission time for the patient, wherein the readmission time is a difference in time between the first HL7 ADT message and the second HL7 ADT message, and instruct a computer of one of the first and the second healthcare providers that generated the second HL7 ADT message to display a readmission notification in real-time with the second HL7 ADT message being received so that the one of the first and the second healthcare providers that generated the second HL7 ADT has immediate access to up-to-date patient information, wherein the readmission notification identifies the readmission based on the comparing, wherein the instructing is executed if, the readmission time for the patient is within a readmission time threshold stored in the memory.

17. The system of claim 16, wherein the first HL7 ADT message is a discharge-type ADT message, and wherein the second HL7 ADT message is an admit-type ADT message.

18. The system of claim 16, wherein the plurality of healthcare providers are distinctly located, owned, and controlled from each other and the computer processor, and wherein the plurality of healthcare providers are connected to a same health information exchange.

19. The system of claim 16, wherein the computer processor is further configured to:

receive a plurality of subscriber parameters from a plurality of subscribers that include the readmission threshold timeframe; and enhance the healthcare information pieces with additional information about the patient, wherein the additional information is from the subscriber parameters, and wherein the processor reads the plurality of healthcare information pieces as enhanced.

20. The system of claim 16, wherein the difference in time between the first HL7 ADT message and the second HL7 ADT message is an amount of time calculated by subtracting a discharge date extracted from the first HL7 ADT message from an admission date extracted from the second HL7 ADT message.

* * * * *